| United States Patent [19] | [11] Patent Number: 4,624,968 |
| Kim et al. | [45] Date of Patent: Nov. 25, 1986 |

[54] MULTI-STAGE FISCHER-TROPSCH PROCESS

[75] Inventors: Chang J. Kim, Bedminster; Rocco A. Fiato, Scotch Plains, both of N.J.

[73] Assignee: Exxon Research and Engineering Company, Florham Park, N.J.

[21] Appl. No.: 814,402

[22] Filed: Dec. 30, 1985

[51] Int. Cl.$^4$ ............................................. C07C 1/02
[52] U.S. Cl. .................................. 518/707; 518/700; 518/717; 585/310
[58] Field of Search ............... 518/706, 707, 700, 717

[56] References Cited

U.S. PATENT DOCUMENTS 4,477,595  10/1984  Madon ................................. 518/715

Primary Examiner—Howard T. Mars
Attorney, Agent, or Firm—Richard E. Nanfeldt

[57] ABSTRACT

A multi-stage catalyst system is disclosed for the production of waxes in a Fischer-Tropsch process while producing relatively low quantities of methane. A first catalyst converts CO and $H_2$ into olefins, while a second catalyst converts the olefin, additional hydrogen and CO into higher molecular weight paraffin.

4 Claims, 2 Drawing Figures

MULTI-STAGE FISCHER-TROPSCH PROCESS

BACKGROUND OF THE INVENTION

This invention is directed at a Fischer-Tropsch process for hydrocarbon production. More specifically, the present invention is directed at a multi-catalyst Fischer-Tropsch process in which CO and hydrogen are contacted by a first catalyst having high olefin selectivities. The resulting olefin, additional CO and hydrogen are contacted with a second catalyst which converts olefins, CO and hydrogen into higher molecular weight products.

Fischer-Tropsch type processes are well known for the production of hydrocarbons from carbon monoxide and hydrogen in the presence of certain catalysts under specific reaction conditions. The specific hydrocarbons produced are dependent on the catalyst utilized and the reaction conditions. The reaction of carbon monoxide and hydrogen to produce hydrocarbons is exothermic. Frequently, it is necessary to maintain the reaction temperature within relatively narrow limits to produce the desired products with a minimum of undesired by-products, such as methane.

In addition, the reactors used for Fischer-Tropsch synthesis typically are relatively large and have relatively low through-put per unit volume. To minimize the production of methane catalysts having relatively low reactivities usually are employed. In addition, the operating conditions in the reactor usually are closely regulated.

U.S. Pat. No. 2,450,500 discloses a multistage Fischer-Tropsch catalyst process utilizing a plurality of reaction zones and different catalysts in which the exothermic heat is utilized to increase the temperature of the flowing gases and of the catalyst in the direction of the flow. Each successive catalyst has a higher optimum reaction temperature than the preceding catalyst. However, the catalysts disclosed are not particularly well-suited for the manufacture of relatively high molecular weight compounds, such as paraffinic compounds having molecular weights in the 72 to 14,000 range.

Therefore, it would be desirable to utilize a process which was operable at relatively high space velocities.

It also would be advantageous to utilize a process which produced relatively large quantities of paraffinic hydrocarbons in the $C_5$ to $C_{100}$ range, while producing relatively low quantities of low molecular weight compounds, such as methane.

It also would be desirable to utilize a process in which accurate temperature control of the system was not critical.

The present invention is directed at a multi-catalyst system in which a first catalyst is utilized to convert hydrogen and carbon monoxide into olefinic compounds and in which a second catalyst is utilized to convert the resulting olefin, and additional quantities of carbon monoxide and hydrogen, into paraffinic compounds.

SUMMARY OF THE INVENTION

The present invention is directed at a process for producing paraffinic hydrocarbons from carbon monoxide and hydrogen comprising:

(b) introducing carbon monoxide and hydrogen into a reaction zone wherein the carbon monoxide and hydrogen contact a first catalyst having a high olefin selectivity; and (b) contacting the resulting olefin with a second catalyst having a high selectivity for converting olefins to heavier paraffinic hydrocarbons.

The above-described Fischer-Tropsch process may be conducted in multiple zones or intermixed in a single zone. The catalyst in each zone may be disposed in a fixed bed, in a slurry or in a fluidized bed. The first catalyst, having a high olefin selectivity, preferably is selected from the catalyst systems consisting of Fe/Ce/Zn/K and Fe/Mn/K and Fe/Co/K. The second stage, having a high selectivity for olefin to higher molecular weight paraffin conversion, preferably comprises a catalyst system consisting of $Ru/TiO_2$, $Ru/SiO_2$, $Ru/Al_2O_3$. The first catalyst and the second preferably are disposed in separate vessels, or in discrete beds within the same vessel, although it may be possible to intermix the first and second catalysts. When the first and second catalysts are disposed in separate vessels or in discrete beds within the same vessel the temperature in the first bed preferably is higher than the temperature in the second bed. The temperature of the first bed preferably should be maintained at a temperature ranging between about 250° C. to about 300° C., while the temperature in the second bed preferably should be maintained at a temperature ranging from about 180° C. to about 220° C. Where the first and second catalysts are disposed in separate beds the space velocity of the reactants contacting the first catalyst zone should be maintained within the range of about 200 to about 10,000. The space velocity of the reactants contacting the second catalyst zone should be maintained within the range of about 100 to about 5,000. The hydrogen:carbon monoxide ratio in the first reaction zone preferably is maintained within the range of about 0.5:1 to about 3.0:1, while the hydrogen:carbon monoxide ratio in the second reaction zone preferably is maintained within the range of about 1.0:1 to about 3.0:1.

Where the first and second catalyst are intermixed in a single zone the temperature preferably ranges from about 220° C. to about 250° C. and the hydrogen:carbon monoxide ratio ranges between about 1.0:1 to about 2:1.

DETAILED DESCRIPTION OF THE INVENTION

Figure 1:
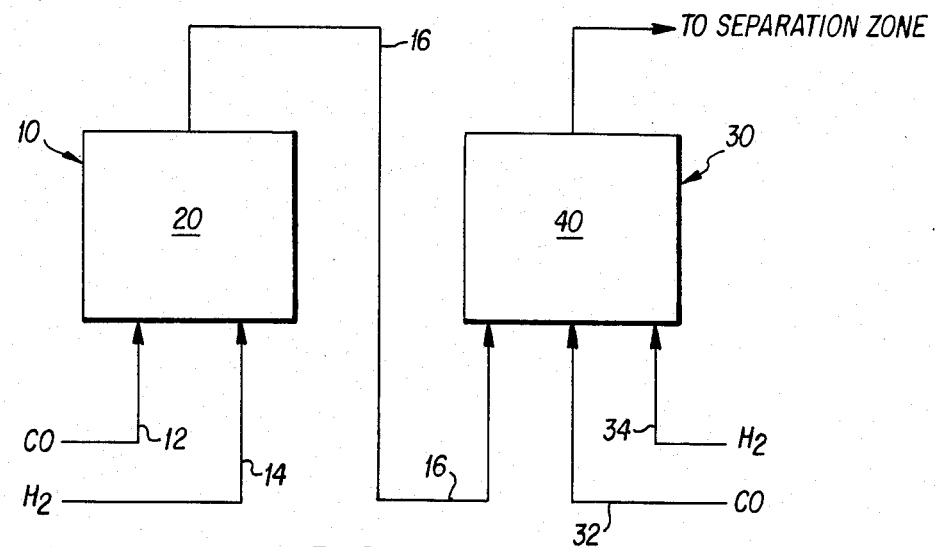
FIG. 1 is a simplified flow scheme of a multi-vessel method for practicing the present invention.

The present invention is directed at the use in combination of a first Fischer-Tropsch catalyst having a high selectivity for converting carbon monoxide and hydrogen into olefins and a second catalyst having a high selectivity for converting olefin, carbon monoxide and hydrogen into higher molecular weight paraffinic compounds. The first Fischer-Tropsch catalyst preferably is selected from catalyst systems consisting of Fe/Ce/Zn/K and Fe/Mn/K and Fe/Co/K.

The preferred first catalyst system comprises Fe/Ce/Zn/K. A detailed description of the preparation and use of this catalyst for Fischer-Tropsch hydrocarbon synthesis is provided in co-pending patent application, U.S. Ser. No. 754,003, the disclosure of which is incorporated herein by reference.

The second Fischer-Tropsch catalyst has a high selectivity for converting olefins, carbon monoxide and hydrogen to higher molecular weight hydrocarbons. Among the preferred catalysts are catalyst systems selected from the group consisting of $Ru/TiO_2$, $Ru/Al_2O_3$, $Ru/Nb_2O_5$, $Ru/SiO_2$.

The preparation and use of $Ru/TiO_2$, Fe/Mn/K and Fe/Co/K catalyst systems are described in U.S. Pat. No. 4,477,595, U.S. Ser. No. 564,465 and U.S. Pat. No. 4,518,707, respectively, the disclosures of which are specifically incorporated herein by reference.

The preparation and use of these catalysts is described as follows:

A preferred catalyst system comprises a first and second catalyst system having the following catalyst compositions.

The first and second catalysts preferably are disposed as discrete beds in one or more vessels. The temperature of the first catalyst is maintained within the temperature range of about 250° C. to about 300° C., preferably within the range of about 260° C. to about 280° C. The pressure in the first catalyst zone is maintained within the range of about 5 to about 20 atm, preferably within the range of about 10 to about 15 atm. The space velocity in the first catalyst zone is maintained within the range of about 200 to about 10,000, preferably about 500 to about 3,000.

The hydrogen:carbon monoxide ratio is maintained within the range of about 0.5:1 to about 3:1, preferably about 1:1 to about 2:1.

The temperature in the second catalyst zone is maintained within the range of about 180° C. to about 220° C., preferably within the range of about 190° C. to about 210° C. The pressure in the second catalyst zone is maintained within the range of about 5 to about 20 atm, preferably about 10 to about 15 atm.

The space velocity in the second catalyst zone preferably ranges from about 100 to about 5,000, preferably from about 500 to about 1,500.

The olefin:carbon monoxide ratio of the reactants entering the second reaction zone is maintained between about 0.01:1 and about 0.5:1, preferably between about 0.03:1 to about 0.2:1, while the hydrogen:carbon monoxide ratio is maintained between about 1:1 and 3:1, preferably between about 1.5:1 and 2.5:1. The ratios of the reactants in the second catalyst zone typically are adjusted by the addition of hydrogen and/or carbon monoxide to the second reaction zone and/or by adjusting the temperature in the first reaction zone.

Referring to FIG. 1, a preferred embodiment for practicing the present invention is shown. A first reaction zone 10 is shown containing a first Fischer-Tropsch catalyst 20 disposed in a fixed bed, fluidized bed or in a slurry. Feed comprising carbon monoxide and hydrogen is shown entering the bottom of zone 10 through lines 12 and 14, respectively. Product from zone 10 comprising olefin, CO and hydrogen is shown exiting the top of zone 10 through line 16 for transfer into the bottom of second reaction zone 30 containing second catalyst 40, which also may be disposed in a fixed bed, fluidized bed or in a slurry. Additional carbon monoxide and/or hydrogen reactants may be added through lines 32, 34, respectively, into zone 30, as necessary. The product and unreacted reactants are withdrawn through line 34, after which the product may be separated via conventional means, such as distillation.

Figure 2:
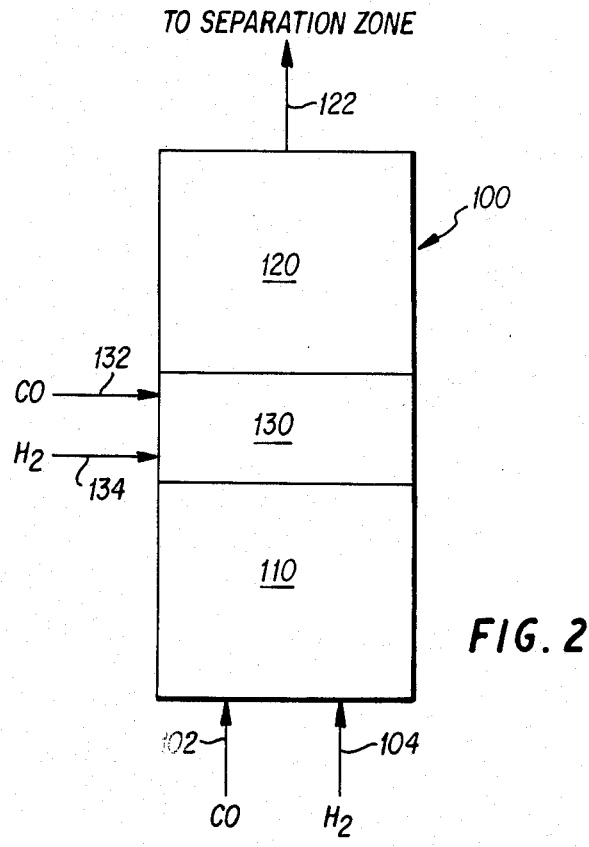
FIG. 2 is a simplified flow scheme of an alternate method for practicing the present invention in a single reaction vessel.

Referring to FIG. 2, another embodiment for practicing the present invention is shown. In this Figure discrete first and second catalyst zones 110, 120, respectively, are disposed in a common vessel 100. The reactants, CO and hydrogen, are introduced into the bottom of vessel 100 through lines 102, 104, respectively. Product from first catalyst zone 110 passes directly to second catalyst zone 120 where olefin formed in the first zone, CO and hydrogen are reacted to form higher molecular weight products which exit through line 122 for separation and recovery of the hydrocarbon via conventional means well known in the art. Additional CO or hydrogen may be added through lines 132, 134, respectively, into the interface zone 130 between zones 110 and 120.

While the use of a single reaction vessel offers certain economies in construction, a multiple vessel design in which the first and second catalyst zones are in separate vessels offers greater flexibility in operation since the temperature, pressure, space velocities and CO:hydrogen ratios in the first and second catalyst zones can be more easily and independently varied if the catalyst zones are disposed in separate vessels.

Where a multiple vessel design is utilized the catalyst may be disposed in a fixed bed, a fluidized bed or in a slurry. The particular method utilized is dependent on many factors, including the catalyst utilized, the required space velocity and heat transfer requirements associated with desired productivity levels. Generally, a slurry bed is preferred since it allows high productivity under isothermal conditions for the first stage olefin synthesis. The second stage contacting $Ru/TiO_2$ is preferably a fixed-bed, which facilitates heavy product isolation.

Where a single vessel is utilized a fixed bed is preferred to prevent undue mixing of the first and second catalyst zones. However, where the operating temperature ranges of the first and second catalyst zones are relatively similar, it may be possible to intermix these in the same vessel.

PREFERRED EMBODIMENTS OF THE INVENTION

The following Example illustrates the present invention without, however, limiting the same hereto.

EXAMPLE

A ⅜" stainless steel down-flow-fixed-bed reactor was charged with two catalysts in series; the top bed containing an Fe/Ce/Zn/K catalyst (24.0 g) which had been previously characterized to give high olefin selectivities (80-85% olefin in $C_2$-$C_4$ range) and the lower bed containing 1.2% $Ru/TiO_2$ catalyst (1.5 g). The catalysts were reduced for 4 hours at 475° C., 100 psi and an $H_2$ flow rate of 200 standard $cm^3/m$. The synthesis reaction was carried out a conditions of 220° C., 6.5 atm., $H_2/CO=1.63$ and a feed gas rate of 36.5 standard $cm^3/m$. The rate and products of the reaction after 4 days on stream are summarized in Table I. The hydrocarbon products, generated by both beds in roughly equal quantities, show a carbon number distribution pattern which differs from a pattern predicted based on a linear combination of data for individual catalyst components (Table II). Thus, the results, when compared to earlier findings with these catalysts, establish that a two-stage bed system gives lower $CH_4$ and $C_2$ selectivities and increased amounts of heavier hydrocarbons.

TABLE I

Fischer-Tropsch Reactions Over Two Stage Beds

Upper Bed: Fe/Ce/Zn/K - 24.0 g

Lower Bed: Ru/TiO$_2$ - 1.5 g +

Quartz Powder - 3.0 g

| | |
|---|---|
| Temperature, °C. | 220 |
| Pressure, atm. | 6.47 |
| H$_2$/CO | 1.64 |
| Flow Rate, std cm$^3$/min. | 36.5 |
| CO Conversion, % | 59.0 |
| CO$_2$ Selectivity, % | 26 |
| CH$_4$ Selectivity, % | 2.5 |
| CO Conversion Breakdown | |
| CO Converted at Upper Bed | 35.0 |
| to Hydrocarbon | 19.6 |
| to CO$_2$ | 15.4 |
| CO Converted at Lower Bed | 24.0 |
| to Hydrocarbon | |
| Hydrocarbon Produced at | |
| Upper Bed | 45% |
| Lower Bed | 55% |
| Gas-Composition at Exit of Upper Bed, atm. | |
| CO | 1.86 |
| H$_2$ | 4.0 |
| C$_2$= | 0.012 |
| 1-Olefins (combined) | <0.06 |

TABLE II

Hydrocarbon Distribution of Products from Two-Stage Beds as Compared with Those from Individual Beds & Linear Combination of Products from Individual Beds

| | | | Two Stage Beds | |
|---|---|---|---|---|
| | Fe/Ce/Zn/K | Ru/TiO$_2$ | Predicted Linear Combination | Observed |
| CH$_4$ | 3.5 | 6.1 | 4.9 | 3.9 |
| C$_2$-C$_4$ | 18.5 | 11.0 | 15.4 | 13.8 |
| C$_5$-C$_9$ | 22.9 | 24.7 | 23.9 | 22.6 |
| C$_{10}$+ | 55.1 | 58.2 | 56.8 | 60.3 |

What is claimed is:

1. A process for producing paraffinic hydrocarbons from carbon monoxide and hydrogen comprising:
   (a) introducing carbon monoxide and hydrogen into a reaction zone wherein the carbon monoxide and hydrogen contact in a first bed a first catalyst having a high olefin selectivity selected from the group consisting of Fe/Ce/Zn/K, Fe/Mn/K and Fe/Co/K; and
   (b) contacting the resulting olefin in a second bed with a second catalyst having a high selectivity for converting olefins to heavier paraffinic hydrocarbons selected from the group consisting of Ru/TiO$_2$, Ru/SiO$_2$ and Ru/Al$_2$O$_3$.

2. A process according to claim 1 wherein the temperature of said first bed is about 250° C. to about 300° C.

3. A process according to claim 2 wherein the temperature of the second bed is about 180° C. to about 220° C.

4. A process according to claim 3 wherein the ratio of H$_2$/CO is about 1.0:1 to about 2:1.

* * * * *